US012357419B2

(12) United States Patent
Quon et al.

(10) Patent No.: US 12,357,419 B2
(45) Date of Patent: Jul. 15, 2025

(54) PROCESSOR CONTROLLED SURGICAL STEP STOOL WITH AUTOMATIC HEIGHT ADJUSTMENT, VACCUM ATTACHMENT, AND ELECTRONIC FOOT SWITCHES

(71) Applicant: Smart Step Surgical LLC, Half Moon Bay, CA (US)

(72) Inventors: Jennifer Lauren Quon, Sunnyvale, CA (US); Frank William Crawford, Half Moon Bay, CA (US)

(73) Assignee: Smart Step Surgical LLC (MONTANA), Billings, MT (US)

( * ) Notice: Subject to any disclaimer, the term of this patent is extended or adjusted under 35 U.S.C. 154(b) by 770 days.

(21) Appl. No.: 17/711,226

(22) Filed: Apr. 1, 2022

(65) Prior Publication Data
US 2023/0310115 A1 Oct. 5, 2023

(51) Int. Cl.
*A61B 90/60* (2016.01)
*E04G 1/22* (2006.01)

(52) U.S. Cl.
CPC .............. *A61B 90/60* (2016.02); *E04G 1/22* (2013.01)

(58) Field of Classification Search
CPC .. A61B 90/60; A61B 2017/00973; E04G 1/22
See application file for complete search history.

(56) References Cited

U.S. PATENT DOCUMENTS

| 3,754,787 | A | * | 8/1973 | Garber | A47C 9/025 297/195.11 |
| 5,158,157 | A |  | 10/1992 | Billington | |
| 5,285,992 | A | * | 2/1994 | Brown | F16M 11/38 248/421 |
| 7,626,132 | B2 |  | 12/2009 | Mezhinsky | |
| D632,101 | S |  | 2/2011 | Sandel et al. | |
| 10,052,764 | B2 | * | 8/2018 | Chelian | B25J 9/1669 |
| 10,503,199 | B1 | * | 12/2019 | Cone | G05G 1/305 |
| 2006/0207021 | A1 | * | 9/2006 | Brunson | A61B 90/60 5/81.1 R |
| 2010/0242174 | A1 | * | 9/2010 | Morrison, Sr. | A61B 90/60 5/507.1 |
| 2015/0008072 | A1 | * | 1/2015 | Knox | B60N 2/162 182/141 |
| 2015/0137567 | A1 |  | 5/2015 | Smith | |
| 2018/0024586 | A1 | * | 1/2018 | Emmerich | G05G 1/30 74/512 |
| 2018/0132958 | A1 | * | 5/2018 | Jochinsen | A61B 34/74 |
| 2019/0117322 | A1 | * | 4/2019 | Laubenthal | A61B 90/92 |

(Continued)

Primary Examiner — Gary C Hoge
(74) Attorney, Agent, or Firm — Stephen E. Zweig

(57) ABSTRACT

Operating room tables have limited height adjustment capability. To adequately treat a patient, surgeons often have to risk back injury and/or stand on rickety piles of prior art step stools, which is unsafe and can compromise sterility. Here, a computer-processor-controlled, motorized, surgical step-platform device is disclosed. The device is configured to have dimensions similar to a step stool. The device is configured to easily slide across a floor to an operating table. Then, often by remote control from a Smartphone, the device can vacuum affix itself into position and automatically raise between 5 to 18 inches above the floor. The device has sophisticated rechargeable battery power management and further accommodates wired, and wireless foot switches to control nearby surgical equipment.

20 Claims, 12 Drawing Sheets

(56) References Cited

U.S. PATENT DOCUMENTS

| | | | |
|---|---|---|---|
| 2022/0160372 A1* | 5/2022 | Hoffmann | A61B 17/00 |
| 2022/0204323 A1* | 6/2022 | Serak | G05G 1/01 |
| 2023/0000272 A1* | 1/2023 | Espino | A47G 27/0231 |

* cited by examiner

PROCESSOR CONTROLLED SURGICAL STEP STOOL WITH AUTOMATIC HEIGHT ADJUSTMENT, VACCUM ATTACHMENT, AND ELECTRONIC FOOT SWITCHES

BACKGROUND OF THE INVENTION

Field of the Invention

This invention is in the field of adjustable stools and automated surgical equipment.

Description of the Related Art

To prevent back injury and degeneration, surgeons must position themselves ergonomically during long surgeries. However, surgeons, their assistants, and surgical technicians also need to optimize their positions around the surgical table to visualize essential patient anatomy, leverage surgical tools and equipment, and compensate for differences in the surgeon's heights. Thus, surgeons face a constant conflict between avoiding personal injury and optimizing patient treatment.

Unfortunately, surgical tables (such as operating tables) are limited in their height adjustment parameters. They often cannot be adjusted to the heights needed for surgeons to perform a given surgery effectively. To optimize visualization and equipment use, surgeons will often stand on step stools throughout the entire operative case. In a typical surgery, at least one member of the operating team will require 1-3 steps due to height discrepancies amongst team members. Surgical step stools, produced by Pedigo Products, Vancouver Washington, and other manufacturers, are thus a widespread piece of equipment in the operating room. Surgeons from all subspecialties use them.

Current step stools vary in material (plastic, metal, etc.), structure, and size/weight but are non-adjustable. They are similar to the types used in warehouses and kitchens to reach high shelves. Therefore, steps are stacked if additional height is required. For example, a Pedigo stackable footstool will typically have a height of about six inches, a depth of about 14 inches, and a width of about 19 inches. It is common to stack between one to three footstools on top of each other to achieve heights between 6 inches and 18 inches.

However, if the steps are not stacked properly, they can be unsteady while surgeons stand on them. Some prior art step stools include handles that allow the steps to interlock side-by-side to increase safety and sturdiness for the surgeon standing on the step. These features also make the surgical step stools easier for staff to pick up and maneuver.

Surgeons typically use several (2-3) ancillary electrical pedal switches connected to operating room equipment and surgical tools during surgery. These tools include high-speed drills, electrocautery apparatus, harmonic bone scalpels, and other equipment types. These foot pedals need to be within range of the surgeon's feet. If the surgeon is standing on a step, they will need additional platform space to accommodate these pedal switches. As a result, multiple prior art step stools may be placed or stacked side-by-side to get this space.

Often, a surgeon may need to combine 4-6 different step stools to accommodate the height and platform space required to control multiple pedal switches. The other staff members must move and stack these steps each time a surgical team member moves around the operative table. This can create a workplace hazard.

Another problem is that pedal switches are often accidentally kicked off these step stools. A non-sterile team member (circulating nurse or other operating room staff) must place the pedal back onto the platform when this happens. This practice increases the chance of contaminating the surgical field as non-sterile team members encroach upon the sterile field (within 1-2 feet) to adjust these pedals. The cords connecting these pedals can also become tangled as the pedals are moved and angle adjusted.

Examples of prior art step stools with handles include Sandel and Ramon D632,101. Brown taught a motorized adjustable step stool in U.S. Pat. No. 5,285,992.

BRIEF SUMMARY OF THE INVENTION

The invention is based, in part, on the insight that what is needed is an improved automatically adjustable standing platform to optimize surgical performance and operating convenience. Ideally, such a platform should be automatically or semi-automatically height-adjustable (such as between about 5" high to 15" high, or 6" high to 18" high) and accommodate (either directly, such as by having somewhat wider dimensions such as 17" deep and 27" wide, and/or via an optional "kick-out" platform) various pedal foot-switches to control operating room equipment. Such a platform would support surgeons and surgical assistants while performing surgery.

In this disclosure, the terms "step-platform" and "step-stool" will occasionally be used interchangeably.

As will be discussed, in some embodiments, the invention may be a computer-processor-controlled, motorized, step-platform device. The invention is configured to have dimensions similar to a step stool, and to elevate the operator (often surgeon or surgical assistant) to various distances, such as between about 5 inches and 18 inches, above the operating room floor, thus enabling the operator (surgeon), often while operating on a patient on a surgical table such as an operating table, to easily adjust for operator-to-operator variations in height or other operator body dimensions (e.g., arm length, lower limb dimensions, and the like).

This step-platform device can comprise a lightweight (under 30 pounds, and usually under 20 pounds) motorized step-platform device. For easy cleaning, operating room floors are usually smooth and usually lack bumps or crevices. The underside of the invention's step platform may have at least some areas configured with smooth plastic or metal that serve as low friction skids even without any optional wheels. Due to its light weight, the invention's step-platform device can be moved or skid along smooth (flat and uncarpeted) floors by one person (either pushing or carrying), and will often be initially placed in a first desired position proximate a table such as an operating table. Here assume that the invention's step platform will be moved while in a contracted form (e.g., only about 5 to 7 inches high).

As will be discussed in more detail shortly, the invention's motorized step-platform device will typically comprise at least one processor (often an ARM-based, x86 based, 8051 based, or other type microprocessor or microcontroller). The step-platform device will also typically comprise memory (often RAM, or FLASH memory), any of a wired or wireless data interface, a motorized height adjustment device (usually at least one processor controlled motor or other type electronic actuator, along with ancillary mechanical devices to translate motor/actuator movement into a step-stool height adjustment), a top-plate (preferably a customizable top plate, that can be configured to hold one or more electronic pedal switches), and optionally, often at least one motorized bottom suction device. Although optional, this suction device can be activated during use, and can significantly reduce the chance that the step-platform device will accidentally move during use.

The invention's step-platform device can be configured to raise and lower, typically between about 5" and about 18" high, using at least one processor-controlled motor and either external commands (e.g., commands sent by direct input onto a data interface such as various switches or touch-screens mounted on the step-platform device itself, a wired computer interface such as a USB interface, or a wireless transceiver configured to receive wireless commands sent from local smartphones or other wireless devices), or in response internal commands, such as height adjustment data stored in memory).

To do this, the step-platform device's at least one processor is typically configured to use input from either its internal memory or from its previously discussed data interface to optionally immobilize and then height-adjust the step-platform device to a first preferred height (e.g., the height preferred by a given operator intending to use the step-stool, which may be different from the step-platform device's previous height). This is done by commanding the motorized height adjustment device to adjust the height of the step-platform device. The optional (but preferred) "immobilization" step is done by commanding the step-platform's at least one motorized bottom suction device to generate a partial vacuum against the (smooth) floor. Here "immobilization" means that the step-stool device will adhere to the floor tightly enough that casual application of pressure, such as 100 pounds or less of sideways pressure, will not cause the step-platform device to accidentally move.

After use, it will often be desirable to reconfigure the step-platform to take up less room, and also to move it to a different location for storage or later use. To do this, the step-platform device's at least one processor can be further configured to use input from the data interface to command the at least one motorized bottom suction device to release the partial vacuum. This will cause the device to release its grip on the smooth floor. This in turn enables a much smaller amount of external force, often 20 pounds or less, which can be readily applied by one person, to move the motorized step-platform over the floor to a different location. Additionally, the at least one step-platform processor can be further configured to use input from the data interface, or other source (such as the device memory) to command the motorized height adjustment device to adjust the height of the step-platform to a different height, such as a lower (5 to 7 inch high) storage height.

Other embodiments, including interfacing with various types of electrical foot pedal switches, built-in batteries, power management, and the like will also be discussed.

DETAILED DESCRIPTION OF THE INVENTION

Figure 1:
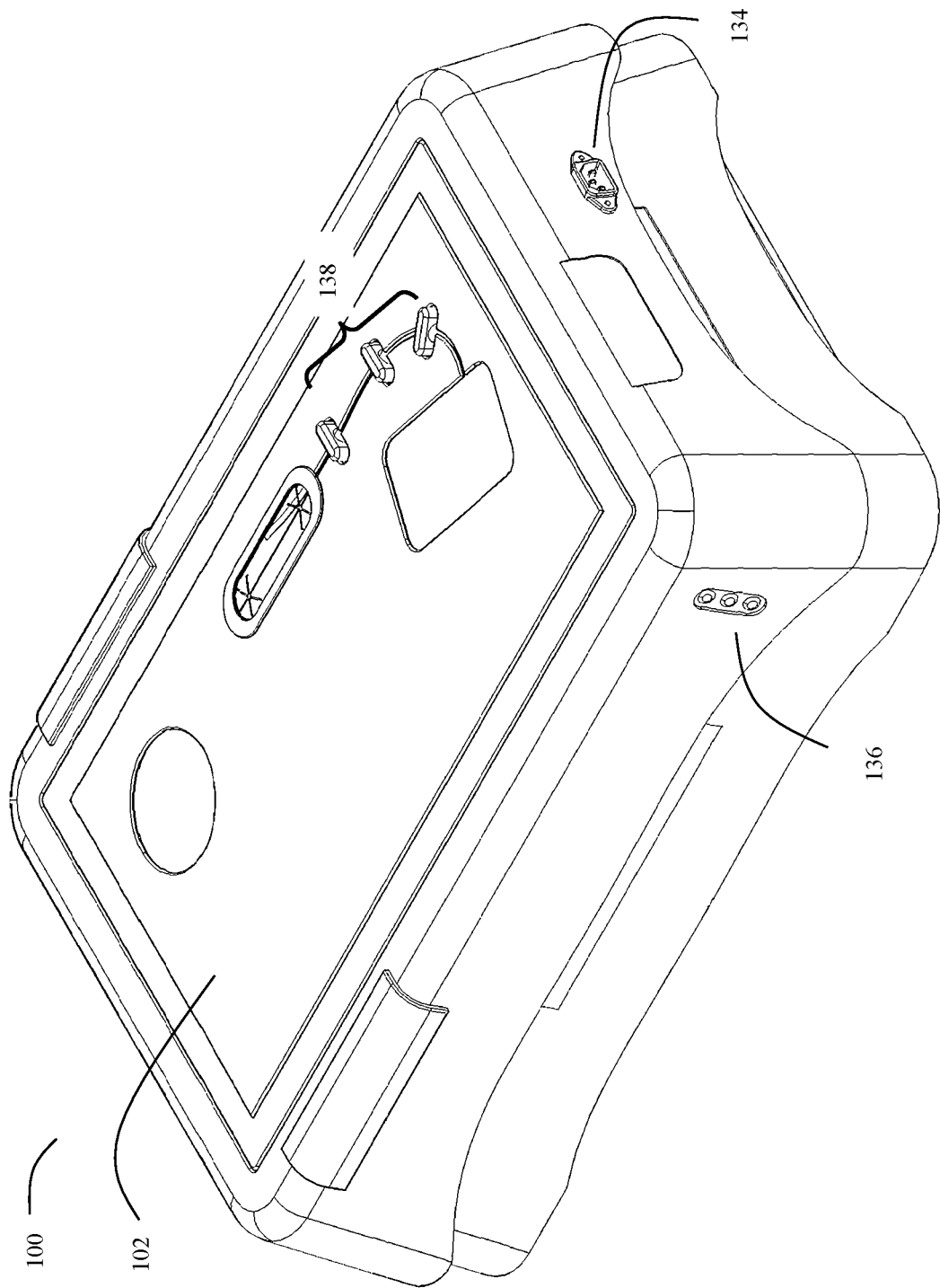
FIG. 1 shows a top view of the surgical step stool (step-platform) in a retracted configuration.

FIG. 1 (100) shows a top view of the surgical step stool (step-platform) in a retracted configuration (100). A top plate (102), AC power input (134, which can be used to either power the step-stool, or recharge the step-stool batteries), and status lights (136, such as LED charge indicator lights) are also shown. See also FIG. 2 to FIG. 5.

An optional cable management system (138), which may comprise various spring-loaded cable claims intended to work with a wired foot switch (see FIG. 5, 212), is also shown. This cable management system (138) functions to provide a plurality of integrated cord traps that are useful for corded foot pedal switches. This helps reduce tangling and clutter from the cords, as well as to help secure the corded foot pedals and prevent them from getting kicked off the platform. An added benefit as this helps improve sterility, as it helps to minimize the number of times that non-sterile personnel need to approach the sterile field.

Figure 5:
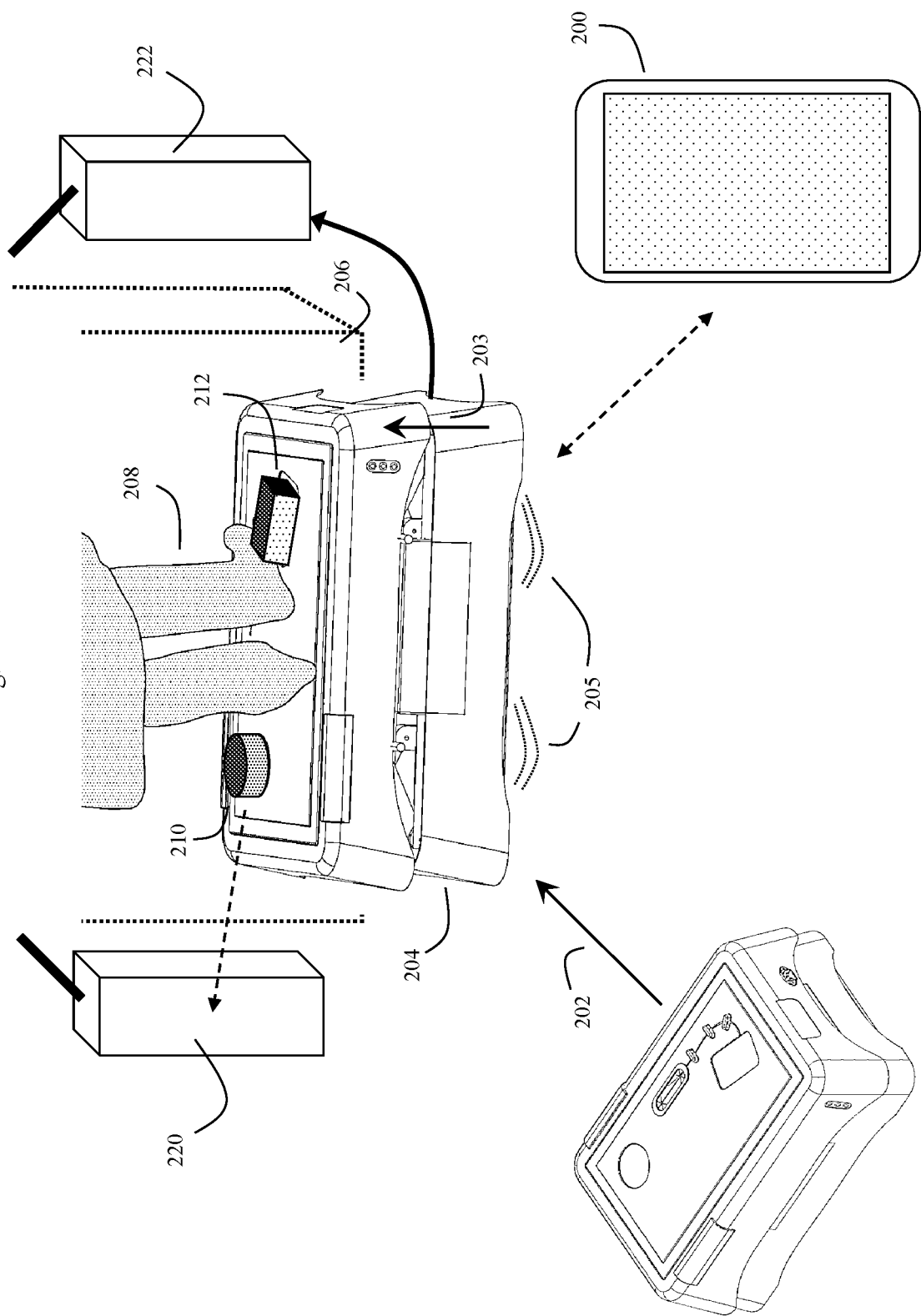
FIG. 5 shows an example of the surgical step stool in use.

In some embodiments, the invention may be a motorized step-platform device (100) configured to adjust to operator-to-operator variations in operator height and other operator parameters. This step-platform device is often referred here as a surgical step stool, or "step stool". This device is lightweight (typically under 30 pounds weight, and preferably under 20 pounds weight for easy mobility). In at least one mode, as shown in FIG. 5, the motorized step-platform device is configured to slide (202) along a smooth floor, such as an uncarpeted operating room floor, by an application of external force (usually human hand or foot force) to a first desired position (204) proximate a table, such as an operating table. The base of this operating table is shown as (206).

Here "proximate" means that a human (208) standing on the step-platform is within arms-length of at least a portion of the table, in other words less than about two feet from the table (206).

Figure 6:
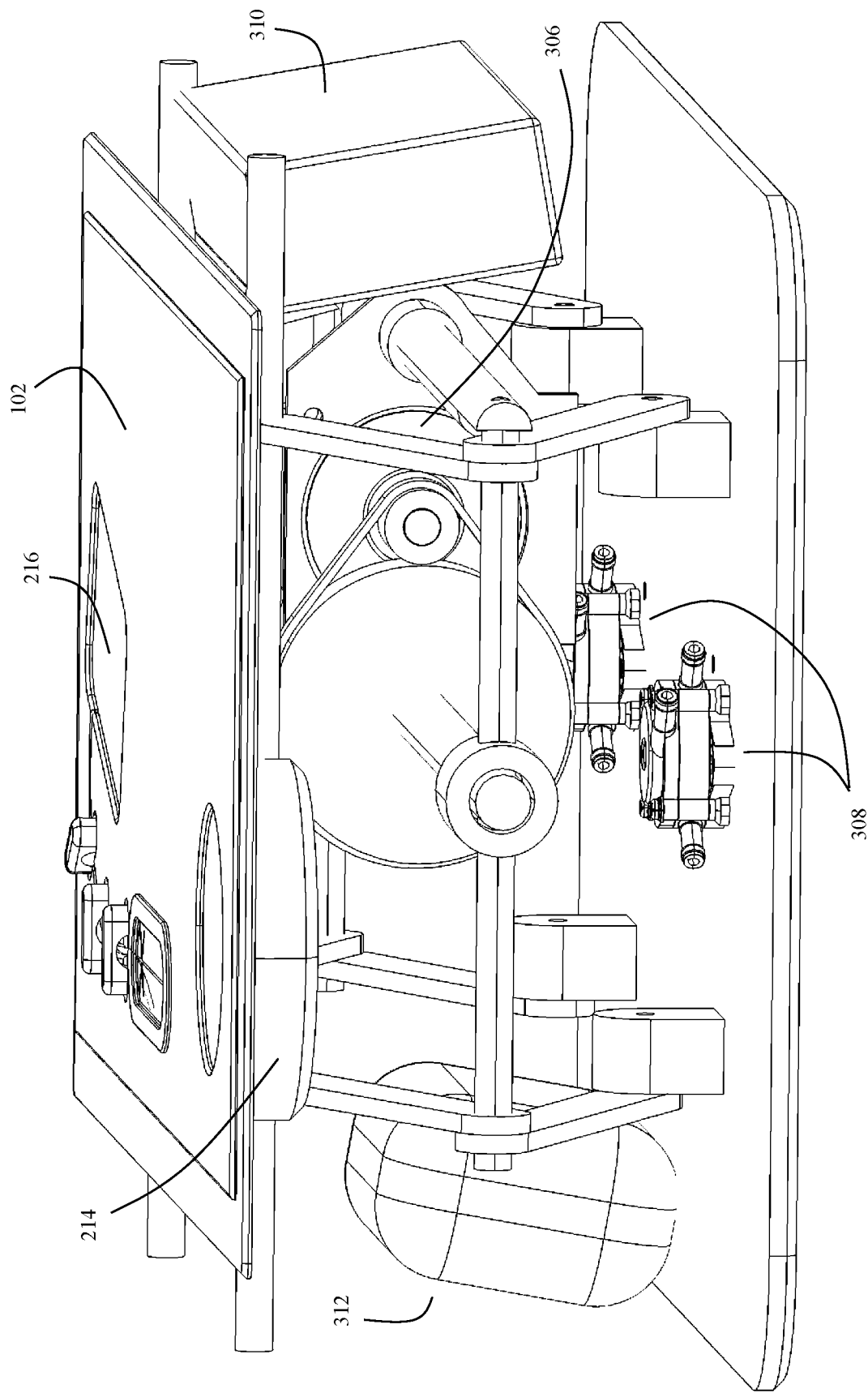
FIG. 6 shows a side view of some of the interior components of the step stool.
Figure 7:
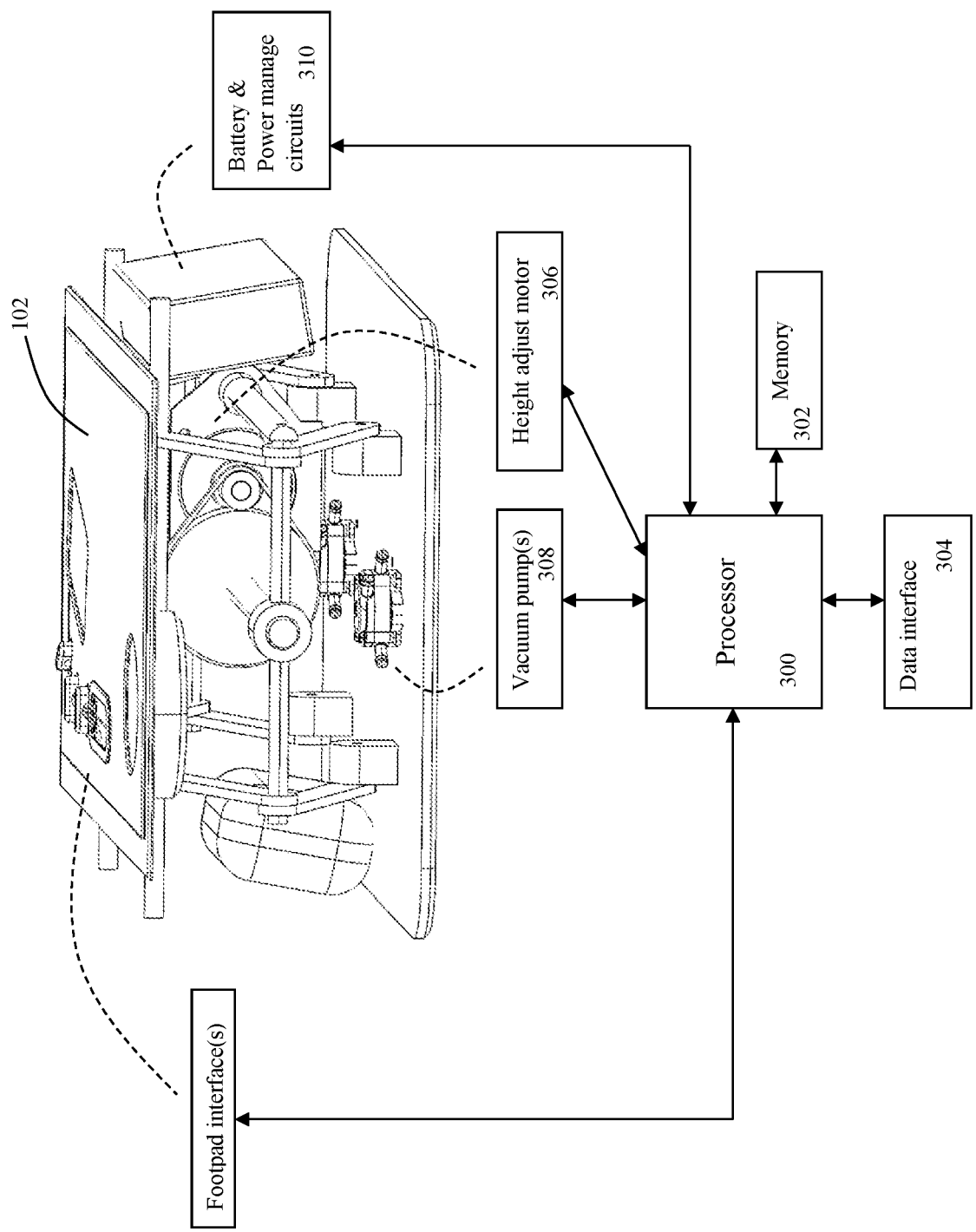
FIG. 7 shows an overview of how the device's processor controls the surgical step stool.

As shown in FIG. 1-5, as well as FIG. 6-7, this motorized step-platform device typically comprises at least one processor (300), memory (302), data interface (here exemplified by a wireless transceiver, such as Bluetooth transceiver 304), motorized height adjustment device (which will usually have at least one height adjust motor 306, along with other mechanical equipment such as belts, gears, lift arms, link rods, and the like), customizable top plate (102), and at least one motorized bottom suction device (see FIG. 2, 130), usually driven by at least one vacuum pump (308).

Figure 4:
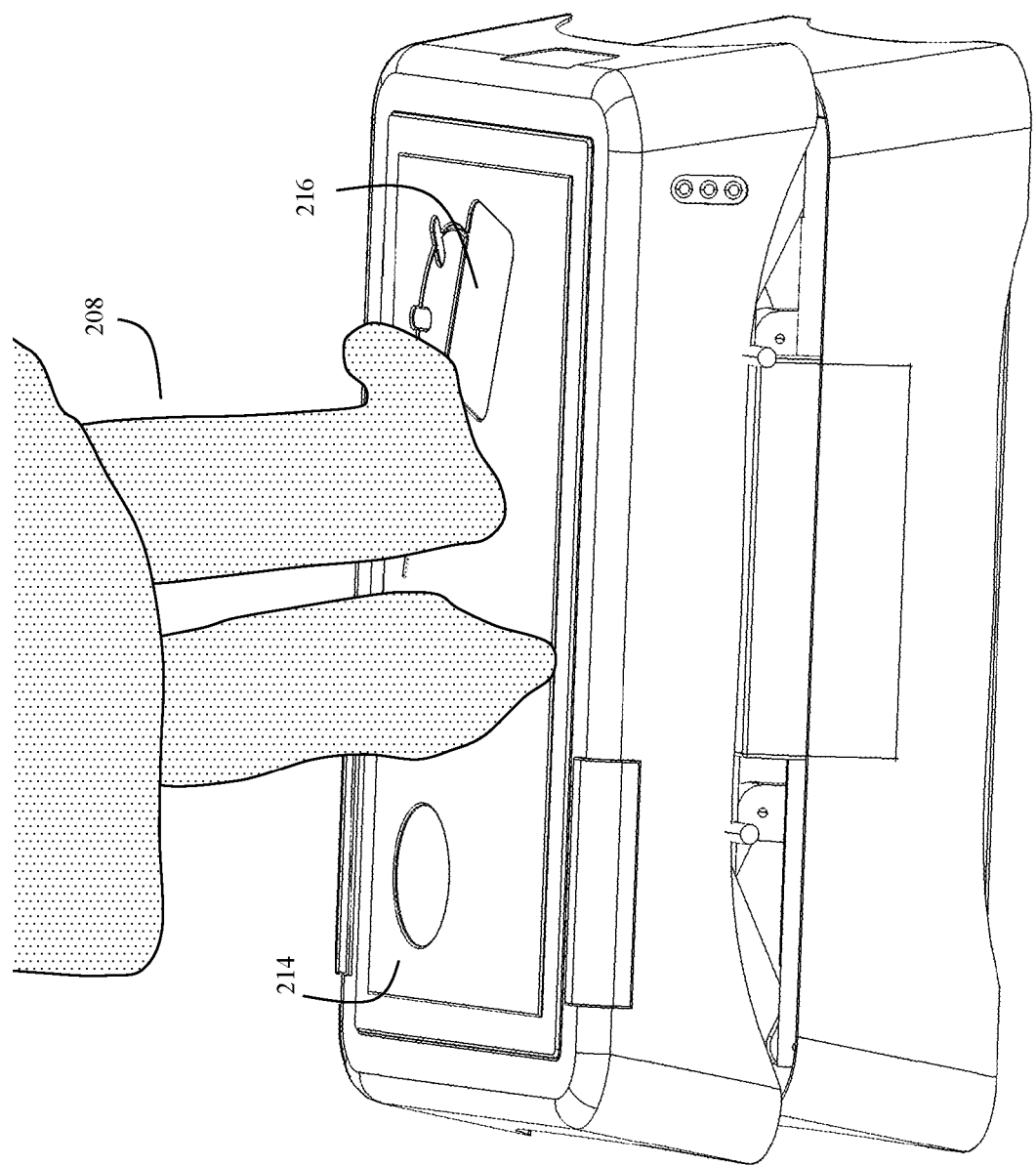
FIG. 4 shows a detail of a human user, such as a surgeon, stepping on top of the surgical step stool.

In some embodiments, the least one processor (300) may be configured (300) to use input from either the computer memory (302) or from the data interface (304) to immobilize and/or height-adjust the step-platform device to a first height. The processor does the height adjust by commanding the motorized height adjustment device (usually by height adjust motor 306) to adjust the height of at least the top plate (102) of the step-platform device. The processor does the immobilization by commanding the at least one motorized bottom suction device (usually by vacuum pumps 308) to generate a partial vacuum against the floor. This fixes the step-stool to the floor so that it will usually take more than 100 pounds of force to move the step stool, thus effectively immobilizing it, and allowing a human operator, such as a surgeon (208), to safely mount the stepstool, as shown in FIG. 4 and FIG. 5, without worry that the step stool might accidentally shift position when someone steps on top of it.

When the user(s) wish to move the step-stool to a different location, the at least one processor (300) is usually further configured to use input from the data interface (304) or an alternative vacuum release switch to command the at least one motorized bottom suction device (often via vacuum pump 308 or computer-controlled release valves) to release the partial vacuum. Once the vacuum is released, the step-stool is no longer tightly bound to the floor. Since it is inherently light weight (usually under 20 pounds), this enables external force (such as human arm or foot force) to move the motorized step-platform over the floor to a different location, such as a storage location, or different location around the table (206). The at least one processor (300) may be further configured to use input from the data interface (304) to command the motorized height adjustment device (usually by height adjust motor 206) to adjust the height of the step-platform to a different height.

Figure 2:
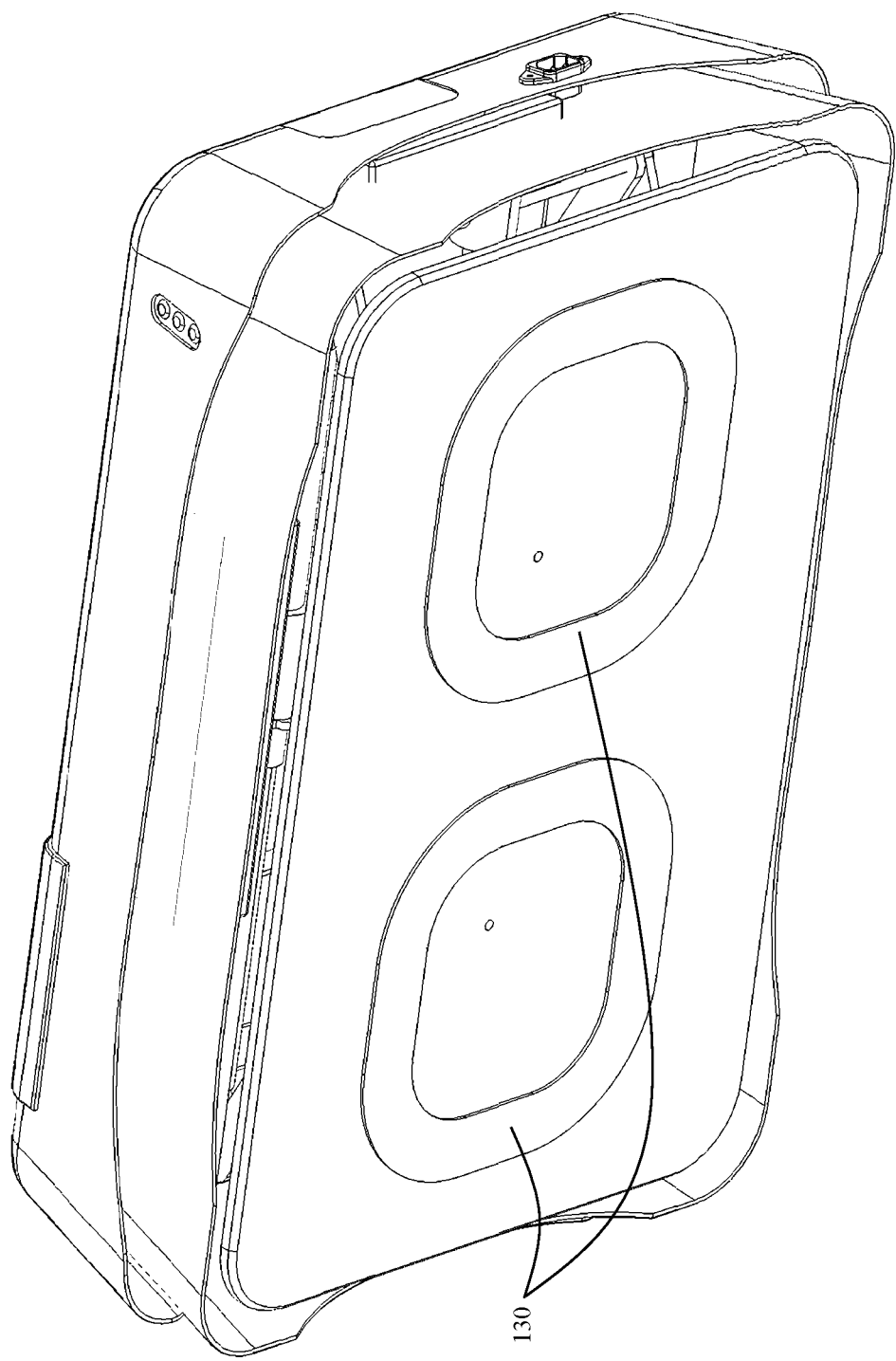
FIG. 2 shows a bottom view of the surgical step stool, showing the bottom suction devices.

FIG. 2 shows a bottom view of the surgical step stool, showing the bottom suction devices (130).

Figure 3:
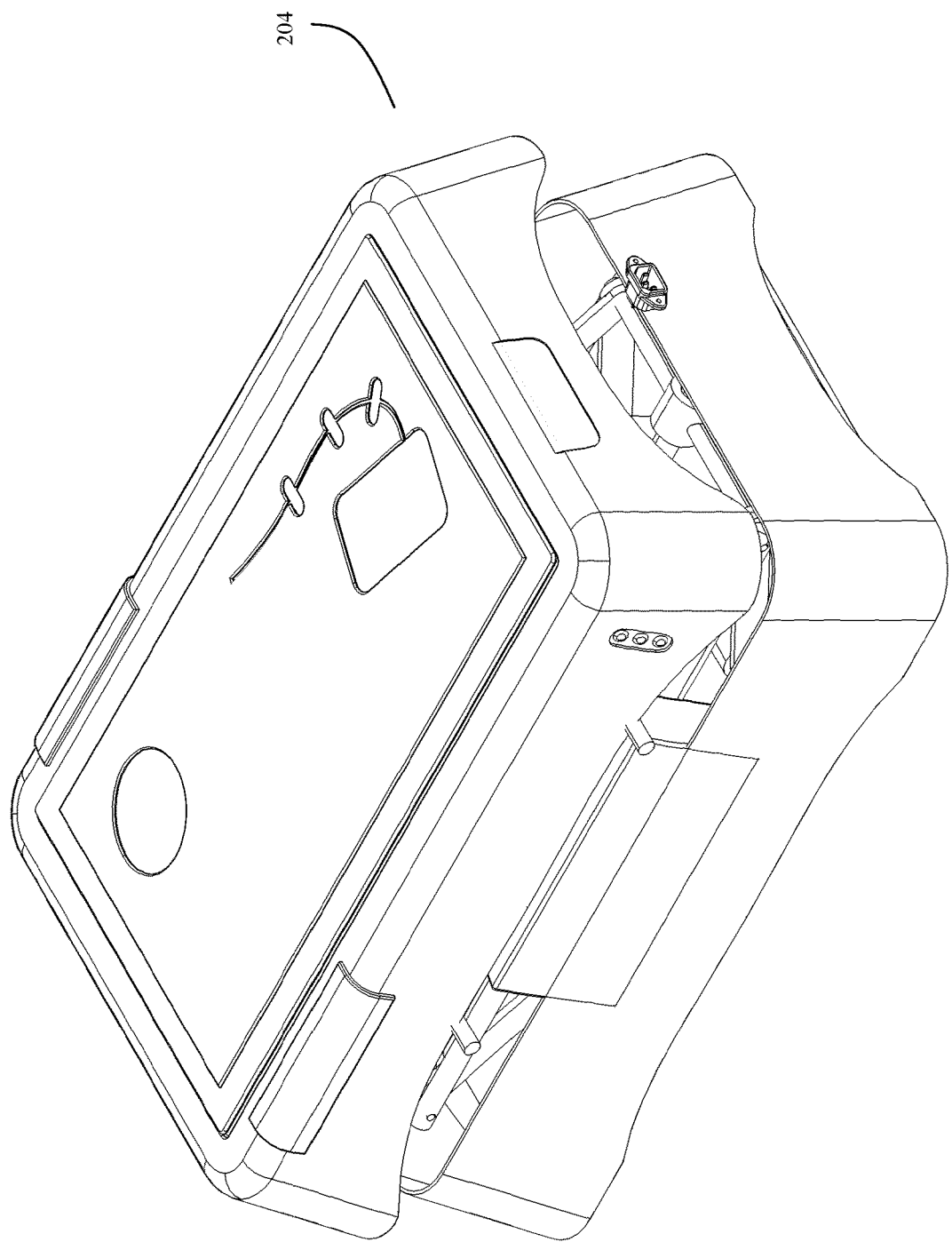
FIG. 3 shows a top view of the surgical step stool in an extended configuration.

FIG. 3 shows a top view of the surgical step stool in an extended configuration (204) that has a height higher than the height previously shown in FIG. 1.

FIG. 4 shows a detail of a human user, such as a surgeon (208), stepping on top of the surgical step stool. The top of this step stool has two defined locations (214, 216) that can accommodate a wireless foot switch (214) or a wired foot switch (216). In some embodiments, at least one wireless foot switch location, such as (214), may further comprise an indictive charging station, such as a Qi or other wireless power transfer unit, to recharge certain types of wireless foot switches.

FIG. 5 shows an example of the surgical step stool in use. Here assume that the step stool was originally stored away from an operating table in an inactive and contracted configuration. The step stool is first moved (202) to a desired location next to an operating table (206). The step stool is then powered on using commands from a data interface (304), often by receiving Bluetooth wireless commands from a suitably configured smartphone (200). The step stool (204) is commanded to affix itself firmly to the floor using the vacuum pumps (FIG. 7, 308) in its bottom mounted motorized suction device (130) to generate a partial vacuum (exemplified by curved dotted lines 205). The step stool is also commanded to raise (adjust its height upward 203). In this example, two different electronic foot switches (210, 212) have been mounted at two defined locations on the footstool's top plate (see FIG. 4, 214, 216). By stepping on these foot switches, the surgeon can then control various types of equipment. This equipment can include operating room equipment, exemplified by (220) and (222).

FIG. 6 shows a side view of some of the interior components of the step stool, including the motor portion of the device's motorized height adjustment device (306), motorized vacuum pumps (308) (part of the device's motorized bottom suction device 130), customizable top plate (102), battery pack (310), and other components, such as an electronics housing (312) that may house the processor (300) and various other electronic components (e.g., 302, 304, etc.)

FIG. 7 shows an overview of how the device's processor (300) controls the surgical step stool's motorized bottom suction device (via vacuum pump 308), motorized height adjustment device (via height adjust motor 306), batteries and power management circuits (310), and other components. The processor may store various settings in memory (302), and can also be controlled using a data interface (304). This can be by wireless connection to an external computerized device such as a smartphone (FIG. 5, 200). The data interface can also include optical or wireless data interfaces, such as USB connectors, electrical switches, built-in-touchpads, touch sensitive screens, keypads, and the like. The data interface can also include various foot or hand activated switches as well.

Expressed in methods format, the invention can also be viewed as a method of configuring equipment (such as an operating room table 206) to adjust to operator-to-operator (208) variations in height and other operator physical parameters.

This method can comprise using external force to slide (202) a motorized step-platform (100) along a floor to a first desired position proximate a table (206). As previously discussed, this motorized step-platform can comprise at least one processor (300), memory (302), data interface (304), motorized height adjustment device (306), customizable top plate (102), and at least one motorized bottom suction device (130, 308).

The method uses the at least one processor (300) and input from either the memory (302) or from the data interface (304) to immobilize (205) and height-adjust (203) the step-platform to a first height by commanding the motorized height adjustment device (306) to adjust the height of the step-platform, and commanding the at least one motorized bottom suction device (308) to generate a partial vacuum against the floor.

According to the method, when desired, input from the data interface (304) and the at least one processor (300) can be used to command the at least one motorized bottom suction device to release the partial vacuum (using by using vacuum pump 308 or a release valve). This breaks the suction that was previously preventing sideways movement, thus enabling the external force to move the motorized step-platform over the floor to a different location (reverse of 202). Further, as desired (and often to either assist in storage or reconfigure for a different user), input from the data interface (304) and the at least one processor (300) can be used to command the motorized height adjustment device (306) to adjust the height of the step-platform to a different height (such as 203).

Although in this disclosure, we will generally refer to the invention as a device, the methods version of the invention is not disclaimed, and it should be readily apparent how the device version and the methods version are essentially one and the same invention.

In some embodiments, the data interface (304) can be any of a wired data interface, such as a universal serial bus (USB), touchscreen, or various step-stool located control switches. Alternatively, or additionally, the data interface (304) can be a wireless data interface, such as a Wi-Fi and/or or Bluetooth wireless transceiver. In a preferred embodiment, the data interface (304) includes at least one wireless transceiver, and the at least one processor (300) and the data interface (304) are configured to receive commands and data from an external computerized device.

For example, in some embodiments, as shown in FIG. 5, the data interface (304) can comprise a wireless Bluetooth transceiver, and the external computerized device can comprise a handheld computerized device (200), such as a smartphone or tablet computer, that itself further comprises a touch-screen and a Bluetooth transceiver.

The processor (300) and data interface (304) can be configured (usually by software stored in memory 302) to operate in various ways. For example, in some embodiments, the at least one processor (300) and the data interface (304) can be configured to transmit or receive operator (that is a user, such as a surgeon or surgical technician) specific parameters from memory (302). These operator specific parameters can comprise operator preferred step-platform height parameters. So, a medium height surgeon may can store "medium extension" step-platform height parameters in memory, while a short surgeon may store "maximum extension" step-platform height parameters in memory. In situations where the data interface (304) is a Bluetooth transceiver, and the processor (300) is configured to receive Bluetooth commands from a suitably configured smartphone (200), then a surgeon or attendant may merely call up a smartphone step-stool app, enter in any security codes as needed, and command the step-stool to extend to "Dr. Smith's previously stored parameters of 13 inches in height."

Figure 8:
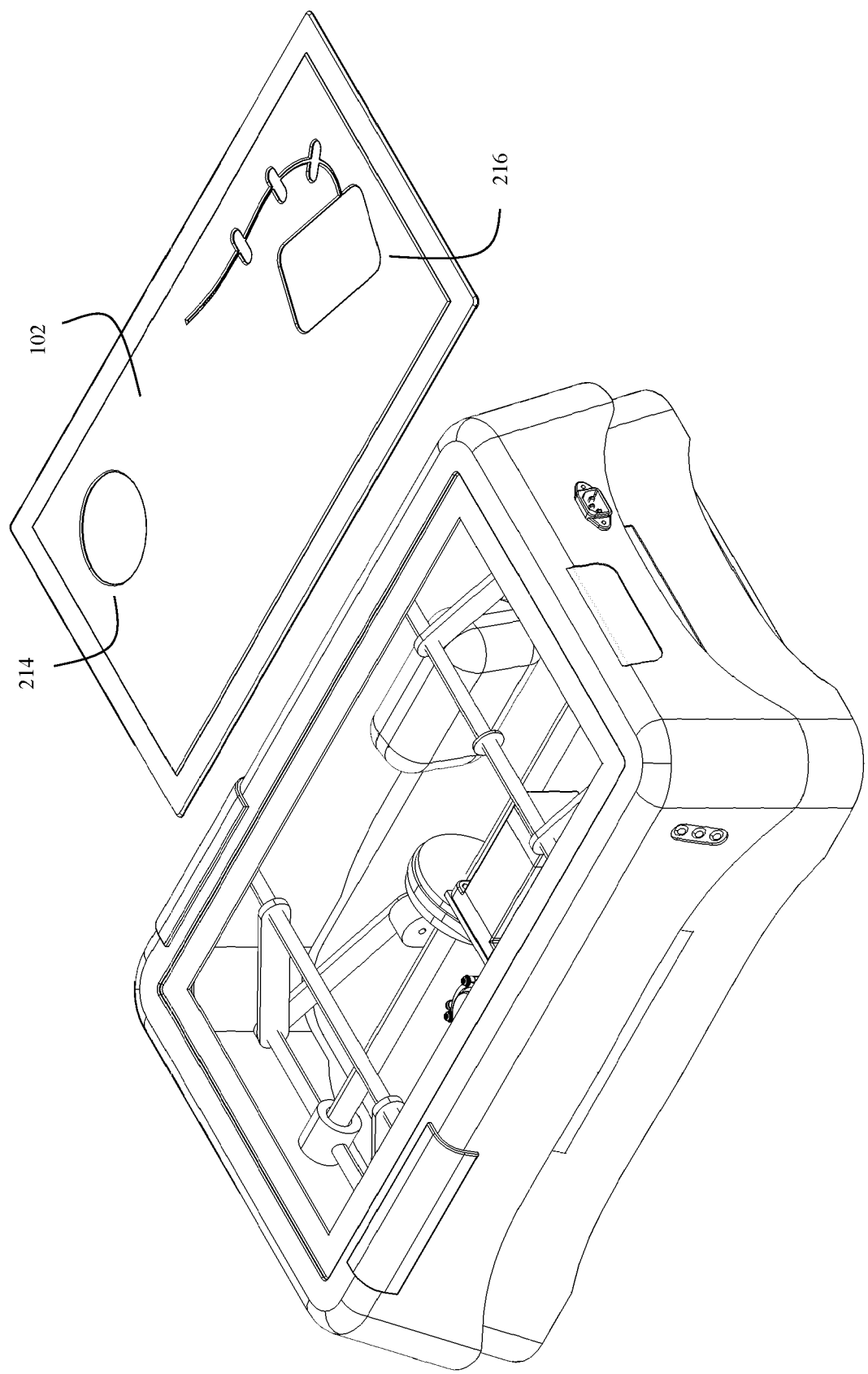
FIG. 8 shows how the customizable top plate may be removed and replaced by an alternative customizable top plate.

FIG. 8 shows how the customizable top plate (102) may be removed and replaced by an alternative customizable top plate. In a preferred embodiment, this customizable top plate (102) and the step-platform are configured to enable toolless (e.g., one-touch, quick release) attachment and detachment of the customizable top plate from the step-platform.

In some embodiments, this customizable top plate may further comprise at least one defined location (such as 214 and 216). These locations are typically configured to interface with an electronic foot switch (such as FIG. 5, 210, 212), that in turn is configured to control at least one item of electronic equipment (FIG. 5, 220, 222).

In some embodiments, the foot switch interfaces (214, 216) can comprise any of a countersunk depth configured to accommodate the electronic foot switch (210), a wireless charger configured to recharge (or supply power to) an electronic foot switch (210), and/or a wired jack or plug configured to receive wired electrical signals from the electronic foot switch (212). Thus, in a common case where the table (206) is an operating table, the electronic foot switches (210, 212) may be configured to control operating room equipment (220, 222).

Figure 9:
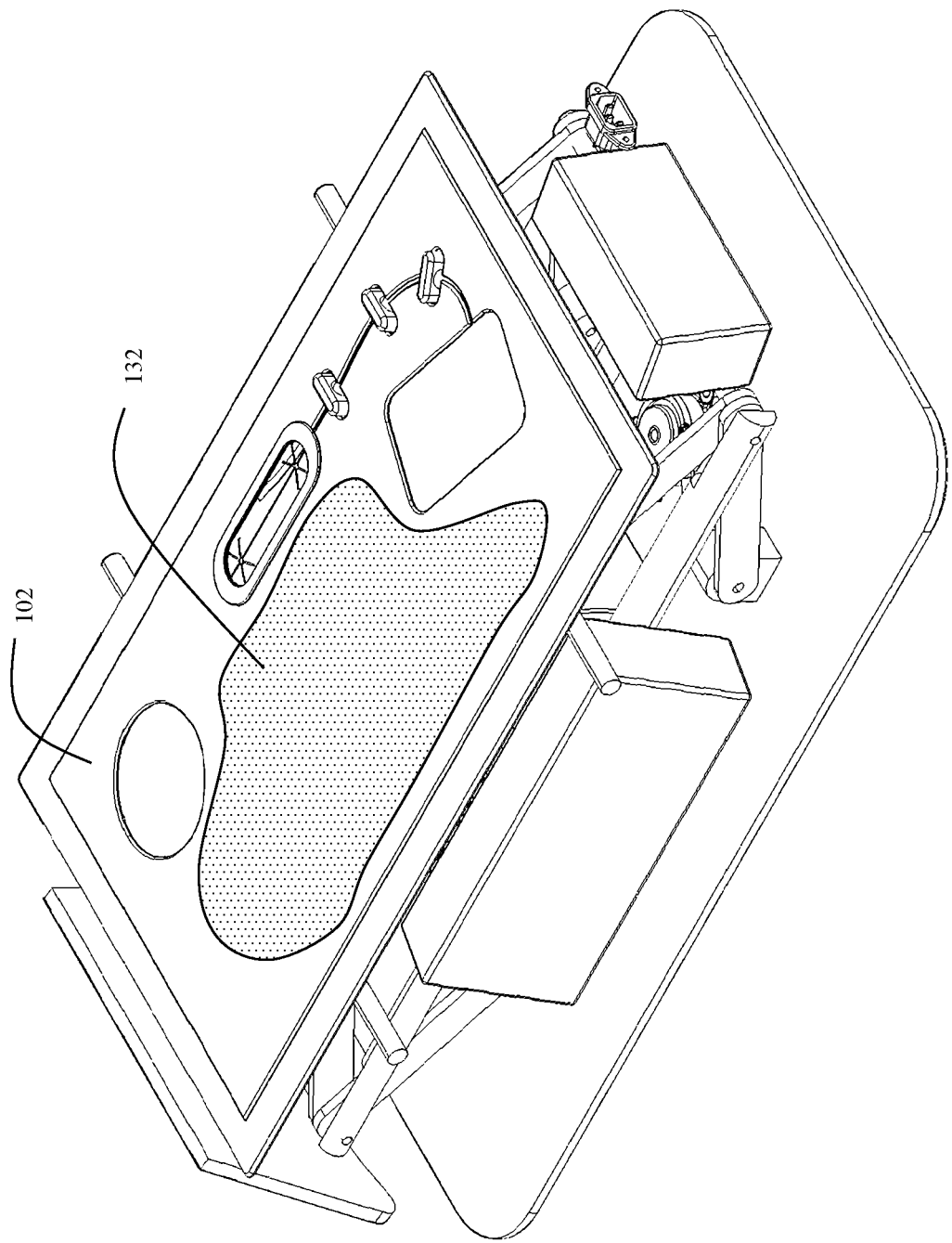
FIG. 9 shows a top view of the step stool with some of the side housing removed.

FIG. 9 shows a top view of the step stool with some of the side housing removed. This figure also shows that in some embodiments, at least a portion of the customizable top plate (102) further comprises an anti-slip mat (132). Such anti-slip mats can comprise a textured surface, often comprising synthetic rubber or other slip resistant material.

Figure 10:
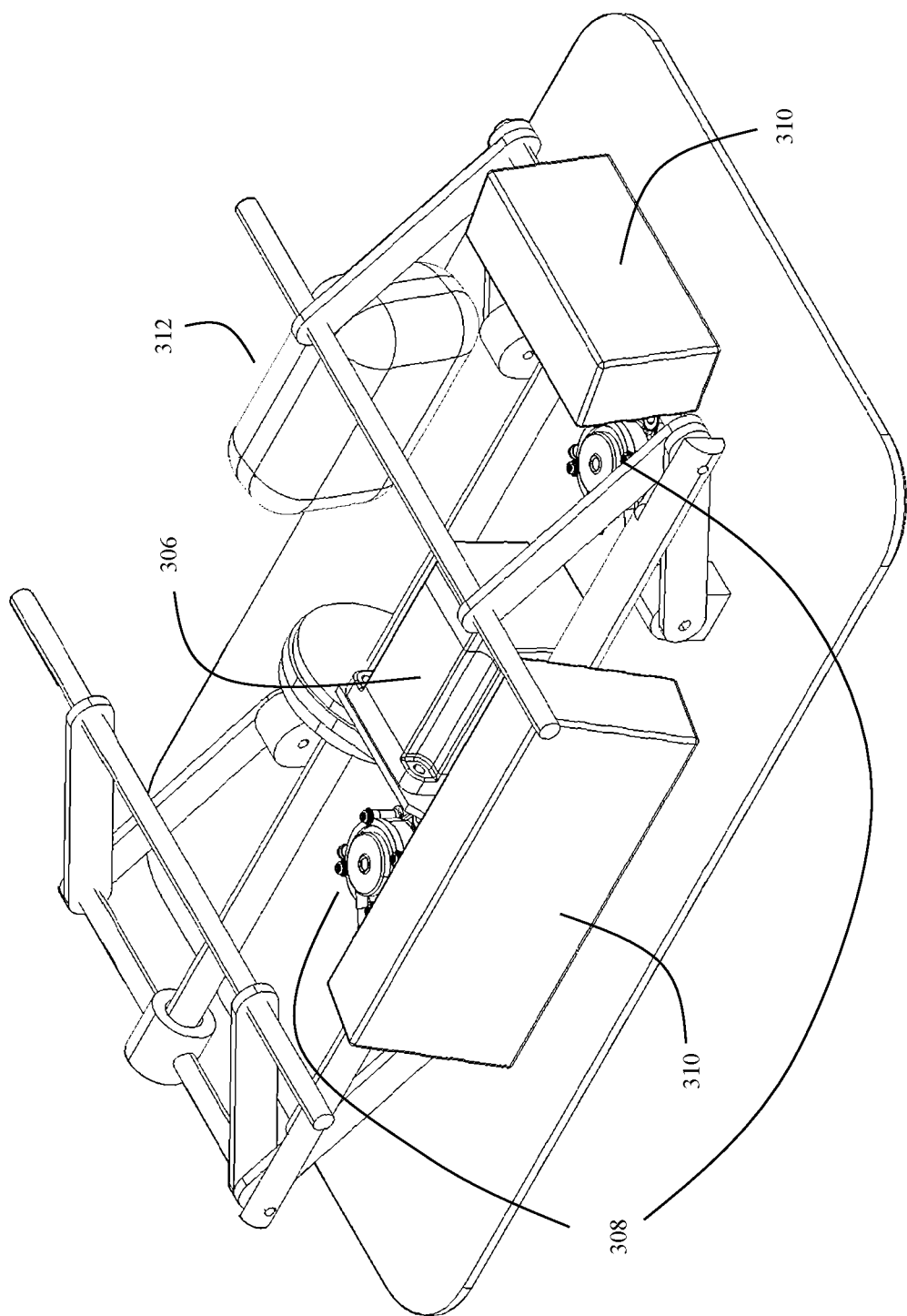
FIG. 10 shows a top view of the step stool with both the side housing and top plate removed.

FIG. 10 shows a top view of the step stool with both the side housing and top plate removed. This exposes more details of the step stool's motorized height adjustment device (e.g., motor 306), motorized bottom suction device (e.g., vacuum pumps 308), battery pack (310) and an optional second battery pack or AC power converter (311), and electronics housing (312). This view also exposes other components of the height adjustment device.

Figure 11:
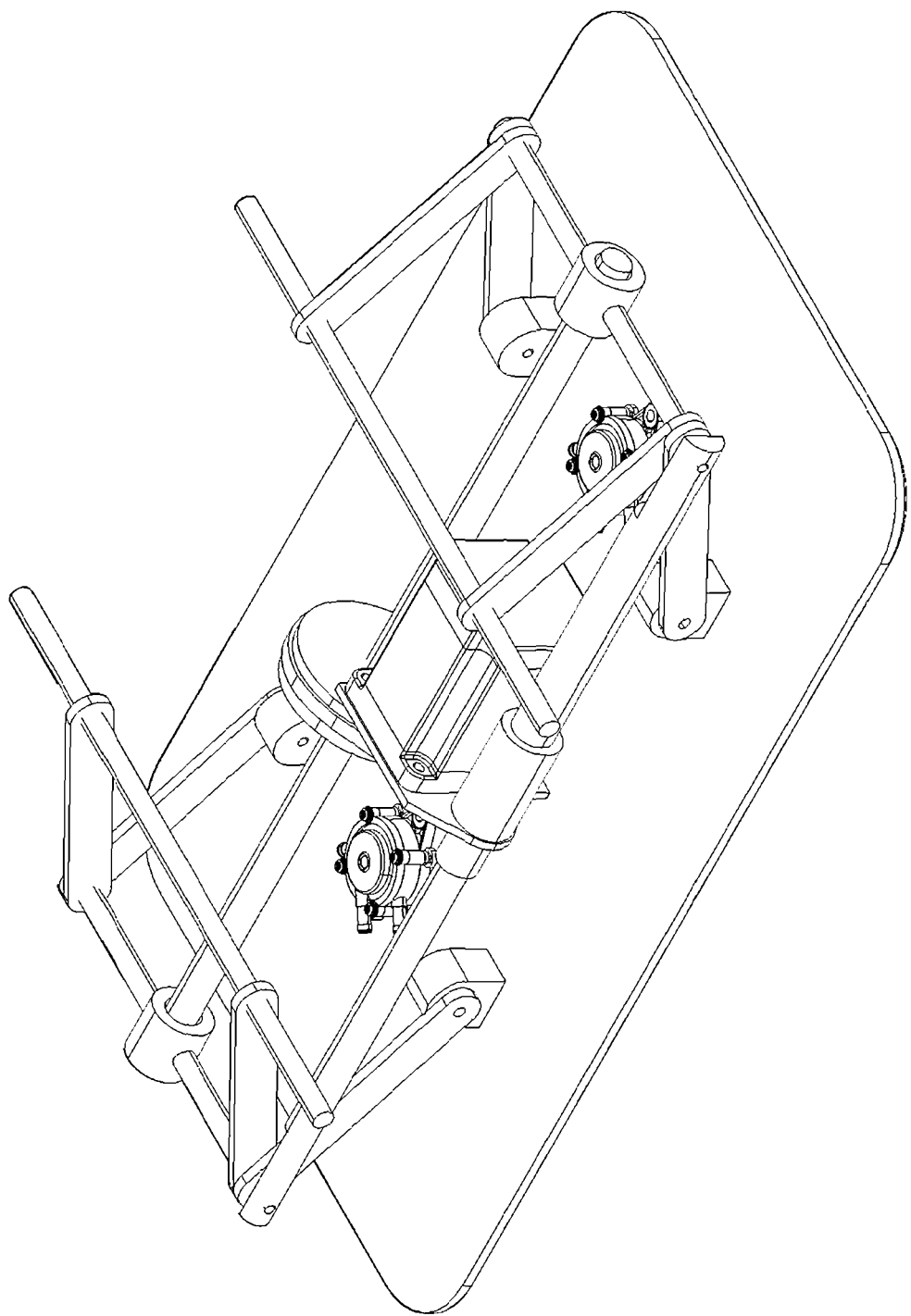
FIG. 11 shows a top view of the step stool with the side housing, top plate, battery pack, and electronics housing removed.

FIG. 11 shows a top view of the step stool with the side housing, top plate, battery pack, and electronics housing removed, exposing more details of the motor and lift link rod components of the motorized height adjustment device, as well as the vacuum pump components of the two motorized bottom suction devices. Examples of such lift rod and motor arrangements may be found in Brown, U.S. Pat. No. 5,285,992, the entire contents of which are incorporated herein by reference.

Figure 12:
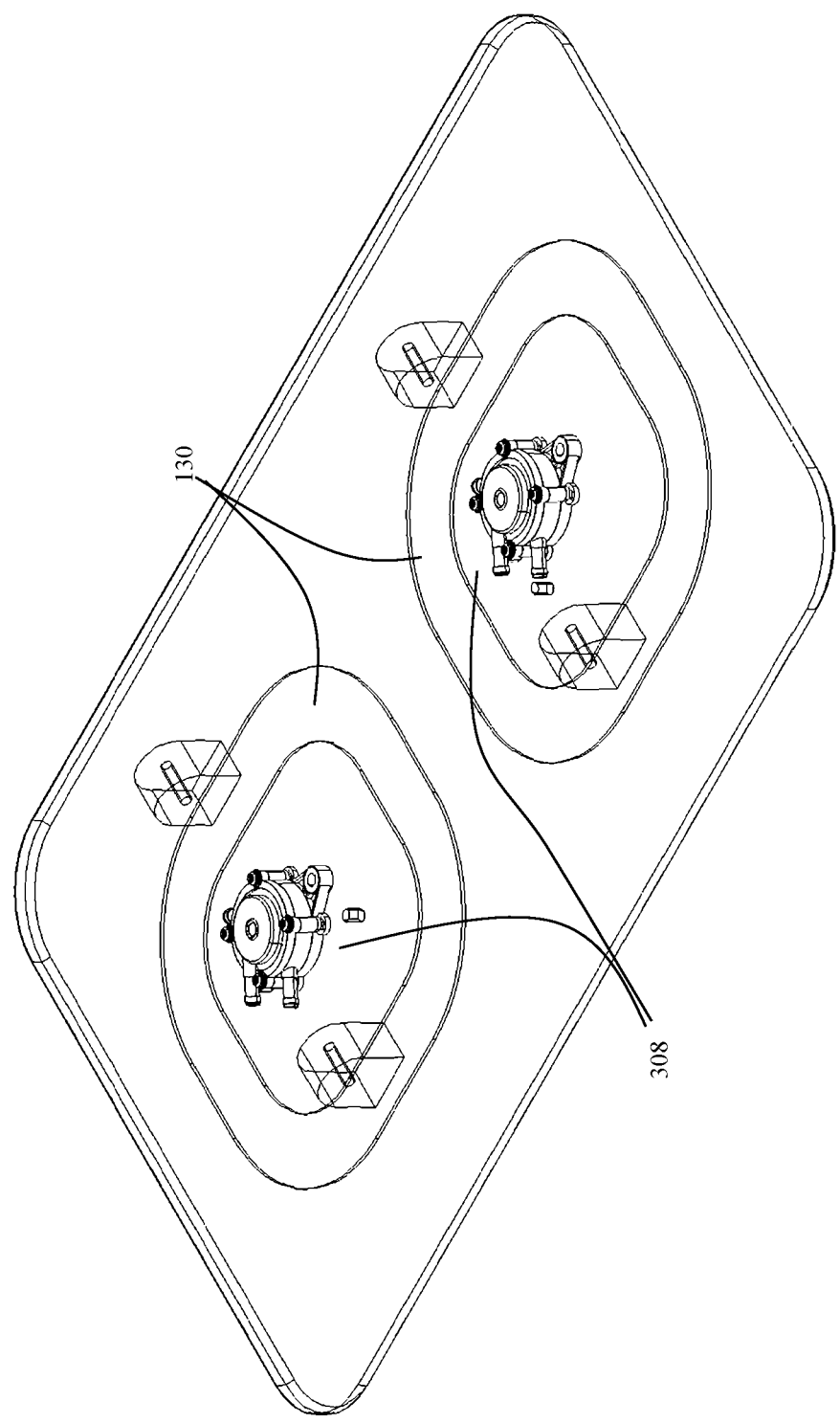
FIG. 12 shows a detail of the position of the vacuum pump components of the step stool's two motorized suction devices.

FIG. 12 shows a detail of the position of the vacuum pump components (308) of the two motorized suction devices (130). In this view, the bottom of the step stool is shown as transparent, enabling the flexible membrane components of the two motorized bottom suction devices (130) to be better visualized. Some base supports of the motorized height adjustment device are also shown.

In some embodiments, the motorized step-platform (100) can comprise at least one rechargeable battery (310), (such as a lithium-ion battery or other type rechargeable battery) and battery access port. In a preferred embodiment, this at least one rechargeable battery and battery access port may be configured to enable toolless exchange of the at least one rechargeable battery.

In some embodiments, the motorized step-platform may also be configured with a second rechargeable battery, with power supply electronics configured to enable a toolless hot-swap of one rechargeable battery while the motorized step-platform is operating with the other rechargeable battery. This would enable battery changes without impact on any of the step-platform height, the motorized bottom suction device, or electronic foot switches. Alternatively, the step-platform may be plugged int an AC electrical outlet via an AC power input plug (134)

In some embodiments, to extend the area of the top plate further, the step-platform may further include one or more hinged fold-out (or kick-out) drop-leaves on either side of the set-platform that can be extended to increase the area of the top-plate when needed, and then can be folded back against the sides of the set-platform when not needed.

The invention claimed is:

1. A motorized step-platform device configured to adjust to operator-to-operator variations, comprising:
   a lightweight motorized step-platform device configured to slide along a floor by an application of external force to a first desired position proximate a table;
   said motorized step-platform device comprising at least one processor, memory, data interface, motorized height adjustment device, customizable top plate, and at least one motorized bottom suction device;
   said at least one processor configured to use input from either said memory or from said data interface to immobilize and height-adjust said step-platform device to a first height by commanding said motorized height adjustment device to adjust said height of said step-platform device, and commanding said at least one motorized bottom suction device to generate a partial vacuum against said floor;
   said at least one processor further configured to use input from said data interface to command said at least one motorized bottom suction device to release said partial vacuum, thus enabling said external force to move said motorized step-platform over said floor to a different location; and
   said at least one processor further configured to use input from said data interface to command said motorized height adjustment device to adjust said height of said step-platform to a different height.

2. The step-platform device of claim 1, wherein said customizable top plate and said step-platform is configured to enable toolless attachment and detachment of said customizable top plate from said step-platform.

3. The step-platform device of claim 1, wherein said customizable top plate further comprises at least one defined location, each said at least one defined location configured to interface with an electronic foot switch configured to control electronic equipment;
   said interface comprising any of a countersunk depth configured to accommodate said electronic foot switch, a wireless charger configured to recharge said electronic foot switch, or a wired jack or plug configured to receive wired electrical signals from said electronic foot switch;
   wherein said table is an operating table, and said electronic foot switch is configured to control operating room equipment.

4. The step-platform device of claim 1, wherein said customizable top plate comprises an anti-slip mat.

5. The step-platform device of claim 1, wherein said data interface is any of a wired or wireless data interface; and
   said at least one processor and said data interface is configured to receive commands and data from an external computerized device.

6. The step-platform device of claim 5, wherein said data interface comprises a Bluetooth interface, and said external computerized device comprises a handheld computerized device further comprising a touch-screen and a Bluetooth transceiver.

7. The step-platform device of claim 5, wherein said at least one processor and said data interface is configured to transmit or receive operator specific parameters from said memory, said operator specific parameters comprising any of operator preferred step-platform height parameters.

8. The step-platform device of claim 1, wherein said motorized step-platform comprises at least one rechargeable battery and battery access port, and said at least one rechargeable battery and battery access port are configured to enable toolless exchange of said at least one rechargeable battery.

9. The step-platform device of claim 8, wherein said motorized step-platform is configured with a second rechargeable battery, and said step-platform device is further configured to enable a toolless hot-swap of said at least one rechargeable battery while said motorized step-platform is in operation without impact on said step-platform height, said motorized bottom suction device, or electronic foot switches.

10. A method of configuring equipment to adjust to operator-to-operator variations, said method comprising:
   using external force to slide a motorized step-platform along a floor to a first desired position proximate a table, said motorized step-platform comprising at least one processor, memory, data interface, motorized height adjustment device, customizable top plate, and at least one motorized bottom suction device;
   using said at least one processor and input from either said memory or from said data interface to immobilize and height-adjust said step-platform to a first height by commanding said motorized height adjustment device to adjust said height of said step-platform, and commanding said at least one motorized bottom suction device to generate a partial vacuum against said floor;
   using input from said data interface and said at least one processor to command said at least one motorized bottom suction device to release said partial vacuum, thus enabling said external force to move said motorized step-platform over said floor to a different location; and
   using input from said data interface and said at least one processor to command said motorized height adjustment device to adjust said height of said step-platform to a different height.

11. The method of claim 10, wherein said customizable top plate has at least one defined location, further affixing an electronic foot switch to at least some of said defined locations, wherein each different foot switch is configured to control different equipment.

12. The method of claim 11, wherein said table is an operating table, and wherein said equipment comprises any of foot switch controlled high speed drills, electrocautery apparatus, and harmonic bone scalpels.

13. The method of claim 11, wherein at least some of said defined locations comprise any of countersunk depth defined locations, and wireless charging locations;
   further using any of said countersunk depth defined locations and wireless charging locations to do any of confine the position of said foot switches, or wirelessly charge said foot switches.

14. The method of claim 11, wherein said customizable top plate is configured to be detachable from said step-platform, further replacing a first customizable top plate with a first set of defined locations with a second customizable top plate with a second set of defined locations.

15. The method of claim 10, wherein said customizable top plate comprises an anti-slip mat.

16. The method of claim 10, wherein said data interface is any of a wired or wireless data interface, further using an external computerized device to transmit commands to said at least one processor.

17. The method of claim 16, wherein said data interface comprises a Bluetooth interface, and said external computerized device comprises a handheld computerized device further comprising a touch-screen and a Bluetooth transceiver.

18. The method of claim 16, further using said data interface to transmit or receive operator specific parameters from said at least one processor and memory, said operator specific parameters comprising operator preferred step-platform height parameters.

19. The method of claim 10, wherein said motorized step-platform comprises at least one rechargeable battery and battery access port, and said at least one rechargeable battery and battery access port are configured to enable toolless exchange of said at least one rechargeable battery.

20. The method of claim 19, wherein said motorized step-platform is configured with a second rechargeable battery, further performing a toolless hot-swap of said at least one rechargeable battery while said motorized step-platform is in operation without impact on said step-platform height, said motorized bottom suction device, or electronic foot switches.

* * * * *